United States Patent
Rosen et al.

(10) Patent No.: US 6,670,348 B1
(45) Date of Patent: Dec. 30, 2003

(54) METHODS AND COMPOSITIONS FOR DESTRUCTION OF SELECTED PROTEINS

(75) Inventors: Neal Rosen, Englewood, NJ (US); Samuel Danishefsky, Englewood, NY (US); Ouathek Ouerfelli, New York, NY (US); Scott D. Kuduk, Harleysville, PA (US); Laura Sepp-Lorenzino, New Haven, CT (US)

(73) Assignee: Sloan-Kettering Institute for Cancer Research, New York, NY (US)

( * ) Notice: Subject to any disclaimer, the term of this patent is extended or adjusted under 35 U.S.C. 154(b) by 0 days.

(21) Appl. No.: 09/403,434

(22) PCT Filed: May 14, 1998

(86) PCT No.: PCT/US98/09805

§ 371 (c)(1),
(2), (4) Date: Oct. 20, 1999

(87) PCT Pub. No.: WO98/51702

PCT Pub. Date: Nov. 19, 1998

Related U.S. Application Data

(60) Provisional application No. 60/046,451, filed on May 14, 1997.

(51) Int. Cl.$^7$ ................. A61K 31/31; A61K 31/35; A61K 31/58; C07D 225/06; C07D 493/12

(52) U.S. Cl. ................. 514/176; 514/27; 514/182; 514/183; 514/450; 514/26; 536/6.4; 552/502; 552/625; 552/638; 540/2; 540/107; 540/109; 540/112; 540/113; 540/115; 540/461; 549/268

(58) Field of Search ................. 514/27, 26, 182, 514/176, 183, 450; 536/6.4; 552/502, 638, 625; 540/2, 107, 109, 112, 113, 115, 461; 549/268

(56) References Cited

U.S. PATENT DOCUMENTS

| | | | |
|---|---|---|---|
| 4,261,989 A | 4/1981 | Sasaki et al. | 424/244 |
| 5,650,430 A | 7/1997 | Sugimura et al. | 514/450 |
| 5,932,566 A | 8/1999 | Schnur et al. | 514/183 |
| 5,968,921 A | * 10/1999 | Gold | 514/183 |
| 6,239,168 B1 | 5/2001 | Ino et al. | 514/450 |

OTHER PUBLICATIONS

Bohen, S.P. "Genetic and Biochemical analysis of p23 and Ansamycin Antibiotics in the Function of HSP90–Dependent Signaling Proteins", Molecular and Cellular Biology, Jun. 1998, vol. 18, No. 6, pp 3330–3339.

Pratt, W.B. "The hsp90–based Chaperone System: Involvement in Signal Transduction from a Variety of Hormone and Growth Factor Receptors", Proceedings of the Society for Experimental Biology and Medicine, Apr. 1998, vol. 217, No. 4, pp 420–434, especially p. 421.

Scheibel, et al, "Two Chapperone Sites in Hsp90 Differing in Substrate specificity and ATP Dependence", Proceedings of the National Academy of Sciences of the USA, Feb. 17, 1998, vol. 95, No. 4, pp 1495–1499, especially p. 1495.

Chen, et al, "The Ah Receptor Is a Sensitive Target of Geldanamycin–Induced Protein Turnover", Archives of Biochemistry and Biophysics, Dec. 1, 1997, vol. 348, No. 1, pp 190–198, especially p. 190.

Landel, et al, "Estrogen Receptor Accessory Proteins Augment Receptor–DNA Interaction and DNA Bending", The Journal of Steroid Biochemistry & Molecular Biology, vol. 63, No. 1–3, pp 59–73, especially pp. 59–61, 1997.

Bamberger, et al, "Inhibition of Mineralocorticoid and Glucocorticoid Receptor Function by the Heat Shock Protein 90–Binding Agent Geldanamycin", Molecular and Cellular Endocrinology, Aug. 8, 1997, vol. 131, No. 2, pp 233–240, especially pp 237–239.

Segnitz, et al, "The Function of Steroid Hormone Receptors Is Inhibited by the hsp90–specific Compound Geldanamycin", The Journal of Biological Chemistry, Jul. 25, 1997, vol. 272, No. 30, pp 18694–18694.

Munster et al., "Inhibition of Heat Shock Protein 90 Function by Ansamycins Causes the Morphological and Functional Differentiation of Breast Cancer Cells", Cancer Research. Apr. 1, 2001, vol. 61, pp 2945–2952.

Schulte et al., "The benzoquinone ansamycin 17–allylamino–17–demethoxygeldanamycin binds to HSP90 and shares important biologic activities with geldanamycin", Cancer Chemotherapy and Pharmacology, 1998, vol. 42, pp 273–279.

Hurst, S. et al., "HSP90 inhibitors block the mitotic checkpoint and are synergistically toxic with spindle poisons", Clinical Cancer Res., Nov. 1999, vol. 8, p. 3788s, #293.

Kherfellah, d. et al, "Effect of the combination of topoisomerase I and topoisomerase II inhibitors on rat glioblastoma cells and drug–resistant variants", Pharmacol. Experimental Therapeutics, Mar. 1999, vol. 40, p. 109, #724.

(List continued on next page.)

Primary Examiner—Richard L. Raymond
(74) Attorney, Agent, or Firm—Oppedahl & Larson LLP

(57) ABSTRACT

Compounds having an ansamycin anitibiotic, or other moiety which binds to hsp90, coupled to a targeting moiety which binds specifically to a protein, receptor or marker can provide effective targeted delivery of the ansamycin antibiotic leading to the degradation of proteins and death of the targeted cells. These compositions may have different specificity than the ansamycin alone, allowing for a more specific targeting of the therapy, and can be effective in instances where the ansamycin alone has no effect. Thus, these compounds provide an entirely new class of targeted chemotherapy agents with application, depending on the nature of the targeting moiety, to treatment of a variety of different forms of cancer. Such agents can further be used to promote selective degradation of proteins associated with the pathogenesis of others diseases, including antigens associated with autoimmune disorders and pathogenic proteins associated with Alzheimer's disease. Exemplary targeting moieties which may be employed in compounds of the invention include testosterone, estradiol, tamoxifen and wortmannin.

40 Claims, 12 Drawing Sheets

OTHER PUBLICATIONS

Stebbins, c. E. et al, "Crystal structure of the Hsp90–Geldanamycin complex: targeting of a protein chaperone by an antitumor agent", *Cell*, Apr. 1997, vol. 89, pp. 239–240 and 246–248.

Rosenhagen, M. C. et al, "Synergistic inhibition of the Glucocorticoid receptor by radicicol and benzoquinone ansamycins", *Biol. Chem.*, Mar. 2001, vol. 382, pp. 499–504.

Chavany, et al. "p185$^{erbB2}$ Binds to GRP94 in Vivo", Journal of Biological Chemistry, vol. 271, No. 9 Mar. 1, 1996, pps. 4974–4977.

Neckers, "Effects of Geldanamycin and Other Naturally Occurring Small Molecule Antagonists of Heat Shock Protein 90 on HER2 Protein Expression", Breast Disease 11 (2000) 49–59. pps. 49–59.

Schnur, et al. "erbB–2 Oncogene Inhibition by Geldanamycin Derivatives: Synthesis, Mechanism of Action, and Structure—Activity Relationships", J. Med. Chem. 1995, 38, 3813–3820.

* cited by examiner

ESTRADIOL-TETHERED-GDM

METHODS AND COMPOSITIONS FOR DESTRUCTION OF SELECTED PROTEINS

This application is a 371 of PCT/US98/09805, filed May 14, 1998 claims the benefit under 35 USC §119(e) of U.S. Provisional Application No. 60,046,451 filed May 14, 1997.

FIELD OF THE INVENTION

This application relates to the use of ansamycin antibiotics as targeted therapeutic agents for the destruction of selected proteins and to novel compositions suited for this use. Destruction of selected proteins in accordance with the invention can be used in the treatment of cancer.

BACKGROUND OF THE INVENTION

Targeted delivery of therapeutic agents as a means for treating cancer has been proposed by many authors. Conceptually, the idea is to deliver a toxic substance selectively to the cancer cells, thus reducing the general toxicity to the patient. This is theoretically possible, since many cancer cell types have been found to have increased levels of hormone receptors and similar receptors. For example, breast cancer cells may have elevated levels of HER2 receptors or estrogen receptors which result in hormone-stimulated growth of cancer cells, while androgen receptors are required for growth of many prostate cancers and mutation of the androgen receptors frequently occurs in advanced prostate cancer.

Hormone receptors have been used in studies on the feasibility of using direct targeted chemotherapy agents to certain classes of cells. Thus, for example, Lam et al., *Cancer Treatment Reports* 71: 901–906 (1987) have reported on estrogen-nitrosourea conjugates as potential cytotoxic agents against human breast cancer, while Brix et al., *J. Cancer Res.* 116: 538–539 (1990) have reported on studies of the use of androgen-linked alkylating agents as antineoplastic agents. See also, Eisenbrand et al., *Acta Oncologica* 28: 203–211 (1989). Myers and Villemez, *Biochem. Biophys. Res. Commun.* 163: 161–164 (1989) have disclosed the possibility of utilizing luteinizing hormone coupled to a truncated diphtheria toxin.

Benzoquinoid ansamycin antibiotics such as geldanamycin and herbimycin A are known to induce the destruction of certain protein tyrosine kinases including HER-2 receptors, insulin and insulin-like growth factor receptors and members of the src-family and *raf* kinase. In addition, benzoquinoid antibiotics can induce the selective degradation in vivo of receptors, including estrogen, androgen and progesterone receptors.

SUMMARY OF THE INVENTION

We have now found that compounds having an ansamycin antibiotic coupled to a targeting moiety which binds specifically to a protein, receptor or marker can provide effective targeted delivery of the ansamycin antibiotic leading to the degradation of proteins and death of the targeted cells. These compositions may have different specificity than the ansamycin alone, allowing for a more specific targeting of the therapy, and can be effective in instances where the ansamycin alone has no effect. Thus, the present invention provides an entirely new class of targeted chemotherapy agents with application, depending on the nature of the targeting moiety, to treatment of a variety of different forms of cancer. Such agents can further be used to promote selective degradation of proteins associated with the pathogenesis of others diseases, including antigens associated with autoimmune disorders and pathogenic proteins associated with Alzheimer's disease.

Compounds in accordance with the invention comprise a targeting moiety which specifically binds to a target protein or cell population, and an ansamycin antibiotic, preferably separated by a spacer. Exemplary targeting moieties which may be employed in compounds of the invention include testosterone, estradiol, and tamoxifen. Preferred ansamycin antibiotics are geldanamycin and herbimycin A.

DETAILED DESCRIPTION OF THE INVENTION

The compounds of the present invention represent a new approach to targeted delivery of chemotherapy to cancer cells. Unlike prior compounds for targeted chemotherapy, which have generally been designed to deliver toxic substances which interfere with cell reproduction, for example by disrupting DNA replication processes, the compounds of the present invention rely on antibiotics which disrupt the normal processing of selected peptides and proteins, including receptors which may be the targets of the compounds of the invention.

Figure 1:
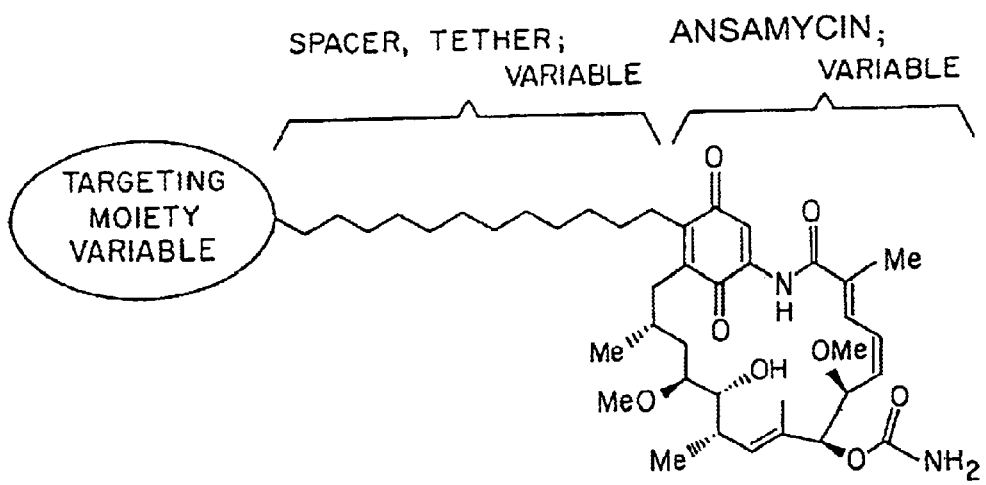
FIG. 1 shows a generalized structure for the compounds of the invention.
Figure 2:
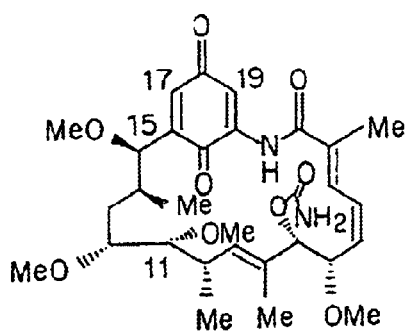
FIG. 2 shows the structure of herbimycin A.

As shown in FIG. 1, the compounds of the present invention comprise a targeting moiety and an ansamycin antibiotic, preferably joined via a spacer bridge to allow flexibility of the two ends of the compound relative to one another. In FIG. 1, the antibiotic moiety is the benzoquinoid ansamycin geldanamycin. However, other ansamycin antibiotics, including herbimycin A (FIG. 2) and macbesin can also be used.

The targeting moiety included in the compounds of the invention is one which will specifically bind to a protein, receptor or marker. The targeting moiety may be a hormone, hormone analog, protein receptor or marker specific antibody or any other ligand that specifically binds to a target of interest. Preferred targeting moieties bind to steroid receptors, including estrogen, androgen and progesterone receptors and transmembrane tyrosine kinases, src-related tyrosine kinases, raf kinases and PI-3 kinases. Specific tyrosine kinases include HER-2 receptors and other members of the epidermal growth factor (EGF) receptor family and insulin and insulin-like growth factor receptors. Examples of targeting moieties include estrogen, estradiol, progestin, testosterone, tamoxifen and wortmannin. Targeting moieties may also be antibodies which bind specifically to receptors, for example antibodies which bind to HER2 receptors as disclosed in International Patent Publications Nos. WO96/32480, WO96/40789 and WO97/04801 which are incorporated herein by reference. Other specific-binding peptides or hormones can also be used as targeting moieties.

The spacer is preferably included to give the molecule the rotational freedom to adapt to the topology of the receptor. Suitable spacers are linear chains having a length of 2 or more atoms, preferably 4 or more atoms. As demonstrated in the examples, the tether length can affect the specificity and effectiveness of the compound. The chains making up the tether will be predominantly carbon, but may include heteroatoms (e.g., N, S, O, or P). The chain of the spacer be functionalized internally, e.g., with a double bond, keto moiety or an amino group, where the heteroatom is outside the linear spacer chain, if additional reactivity is desired. FIGS. 9A–F show the structures of various GM-estradiol compounds with differing tether lengths and functionalization.

The compounds of the invention are useful in the treatment of cancer, where the cancer cells express proteins that interact with the targeting moiety and that are required for viability. Thus, prostate cancer can be treated by administration of a compound with an androgen receptor binding moiety while estrogen receptor positive breast cancer can be treated by administration of a compound with an estrogen-receptor binding moiety.

Breast cancer cells have been found in some individuals to exhibit increased levels of various types of hormone receptors including estrogen receptors and erbB2 (also known as HER2) when compared to non-cancerous cells, and these proteins are important for growth of a significant proportion of breast cancers. GM-E2, a compound in which estradiol is coupled to geldanamycin, has been found to selectively destroy these receptors, and to have less effect on other receptor types (e.g., androgen receptors, other tyrosine kinase receptors and the raf1 kinase) than geldanamycin alone. Thus, GM-E2 can be used to selectively inhibit or destroy breast cancer cells with less toxicity to other cell types.

Wortmannin-tethered ansamycin antibiotics are used to target the antibiotic to PI-3 kinases. PI-3 kinases are found in a variety of cancers. PI-3 kinases are not degraded by exposure to untargeted GM. However, our studies have shown that GM coupled to an isomer of wortmannin which binds to but does not inhibit PI-3 kinases is an active inhibitor of the enzymes. Thus, ansamycin antibiotics can be used in combination with wortmannin to provide a valuable chemotherapy agent for cancer cells expressing PI-3 kinases. Further, this data supports the conclusion that such antibiotics can be used in combination with other species of targeting moiety to inhibit or destroy targeted proteins, even where the targeted protein is not affected by the ansamycin alone. Thus, molecules in accordance with the invention provide therapeutic benefit in cases where the targeted protein is pathogenic.

While not intending to be bound by a particular mechanism, it is believed that the hybrid compounds of the present invention work as a result of an interaction between the ansamycin portion of the hybrid and the chaperone protein hsp90. Hsp90 contains a deep binding pocket that tightly binds ansamycins. When this pocket is occupied by ansamycins, hsp90 forms a stable heterodimer with proteins to which it binds, such as steroid receptors, and these proteins are destroyed. The hybrid molecules described in this invention act as a bridge to create intracellular complexes between hsp90 and the targeted protein, with the ansamycin binding to the hsp90 and the targeting moiety binding to the targeted protein. This results in inhibition of the targeted protein and in many cases in the degradation of the targeted protein. However, because the function of the ansamycin is to provide an association with hsp90, there is no requirement that the ansamycin be directly effective to inhibit or degrade the target protein. Similarly, the targeting moiety need only bind to the targeted protein. It need not inhibit that protein.

From this understanding of the mechanism, it will be appreciated that the present invention is not limited to hybrid compounds containing ansamycins, but in fact encompasses any hybrid compound in which a targeting moiety is coupled to a moiety which binds to the same pocket of hsp90 and thus create the same type of bridge. An example of a non-ansamycin that could be used in place of the ansamycin is Radicicol. Further, there is a family of closely related hsp90-like chaperone molecules which contain binding pockets which are the same as or very similar to the pocket of hsp90 which binds ansamycins. Hybrid drugs which bind to these molecules are also within the scope of the present invention.

The same mechanism which permits targeted inhibition or degradation of PI-3 kinases using ansamycin antibiotic complexes can be applied to the treatment of other diseases where a protein is implicated in the pathogenesis. Thus, ansamycin antibiotics coupled to a targeting moiety which binds to pathogenic proteins associated with Alzheimer's disease could be used in treatment of Alzheimer's disease. Similarly, antigens associated with autoimmune disorders such as multiple sclerosis might be degraded using a targeted ansamycin antibiotic.

Figure 3:
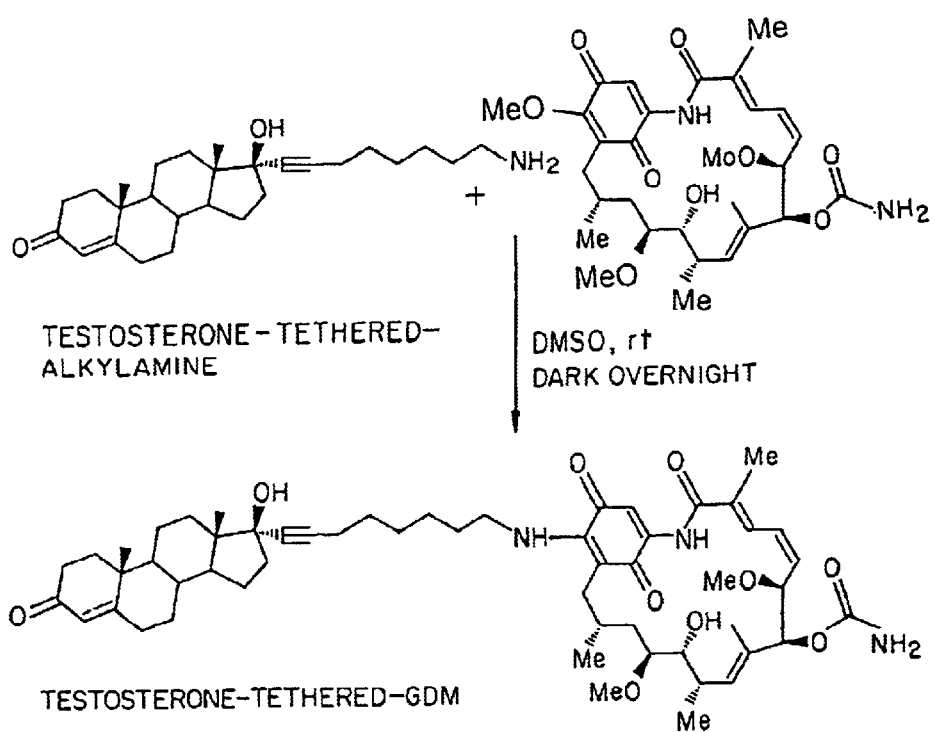
FIG. 3 illustrates the synthesis of a testosterone-geldanamycin compound according to the invention.
Figure 4:
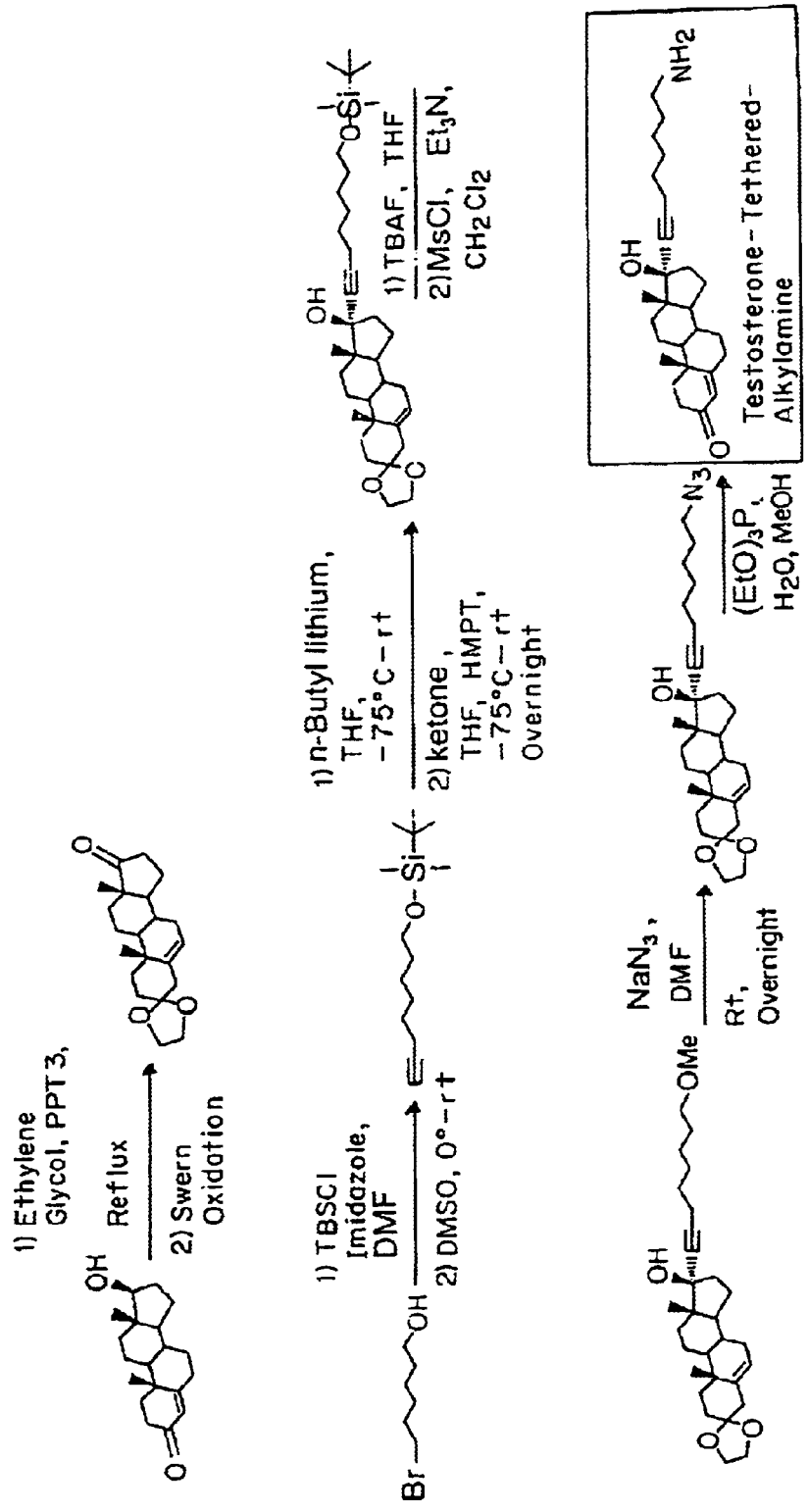
FIG. 4 shows the synthesis of an alkylamino testosterone useful in synthesizing compounds according to the invention.

Synthesis of the compounds of the invention is readily achieved by reacting an primary or secondary amino-derivative of the targeting moiety with the ansamycin antibiotic in DMSO overnight in the dark. Thus, as shown in FIG. 3, a testosterone-geldanamycin product was obtained by reacting a 17-alkylamino testosterone with geldanamycin. The 17-alkylamino testosterone is prepared (FIG. 4) by alkylation of a monoprotected 17-keto testosterone with the lithium acetylide of 8-terbutyldimethylsilyloxy-1-octyne in tetrahydrofuran (THF) and hexamethylphosphorous triamide (HMPT). The resulting silyl ether was transformed into its corresponding mesylate in two steps: desilylation with tetrabutylammonium fluoride and mesylation (MsCl, $Et_3N$, $CH_2Cl_2$). The mesylate was then reacted with sodium azide ($NaN_3$) in dimethylformamide (DMF) at room temperature to give the corresponding azide. Acid hydrolysis of the acetal, followed by triethylphosphite reduction of the azide gave the desired 17-aminoalkyl testosterone in good yield. This was reacted with geldanamycin (GM) in DMSO for 12 hours at room temperature to give 17-testosterone-tethered-17-demethoxy-17-GM as a purple solid. The corresponding reaction using herbimycin A in place of geldanamycin proceeds the same way, albeit somewhat more slowly, to produce two products coupled to the spacer at the 17 and 19 positions in a ration of approximately 3:4.

Figure 5:
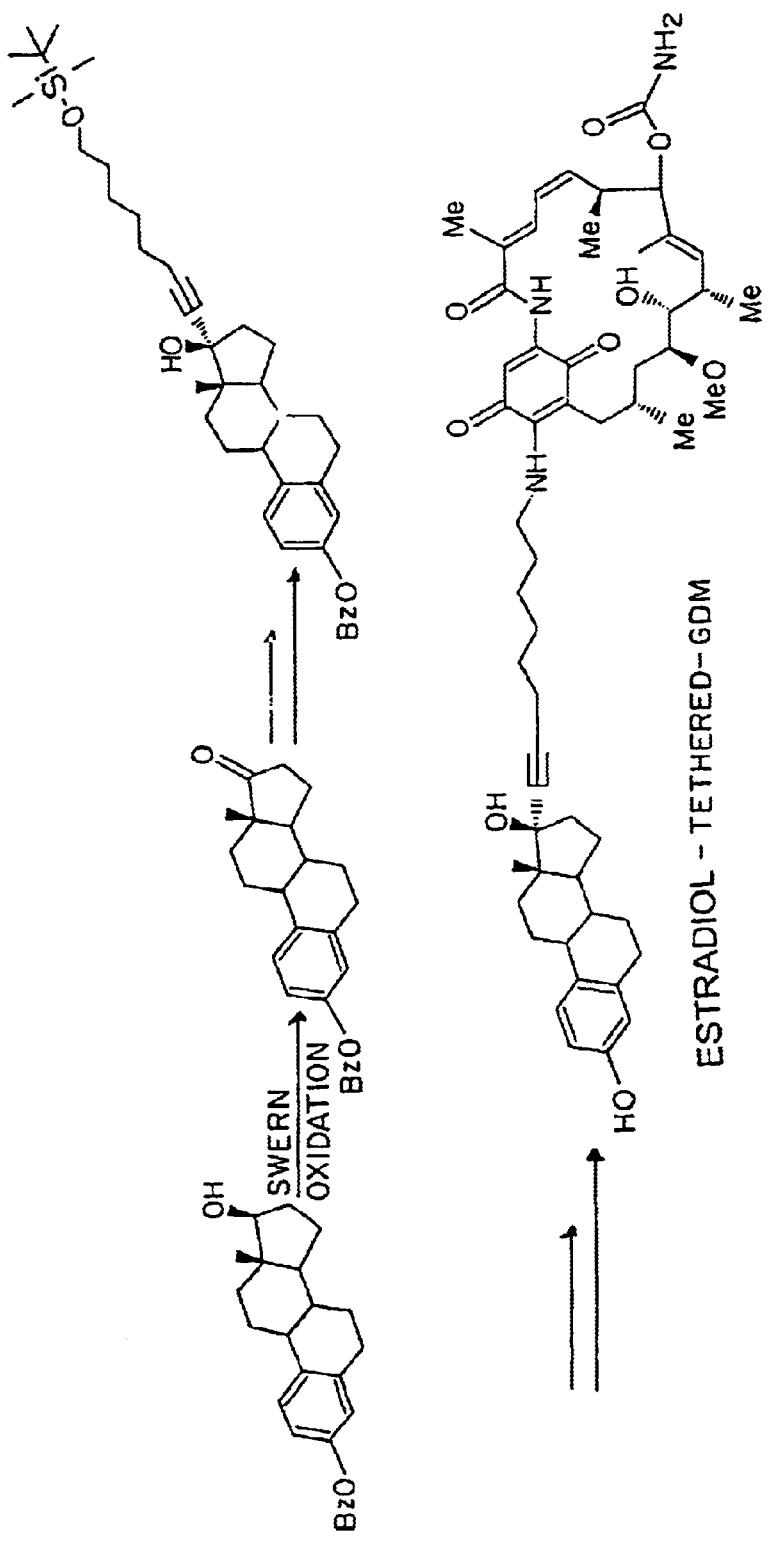
FIG. 5 shows the synthesis of an alkylaminoestradiol/GM compound in accordance with the invention.

FIG. 5 shows the synthesis of an alkylaminoestradiol/GM compound in accordance with the invention. The synthesis is substantially the same as the testosterone synthesis, except that a different protecting group, i.e., a benzyl group, is used on the phenolic hydroxy.

Figure 6:
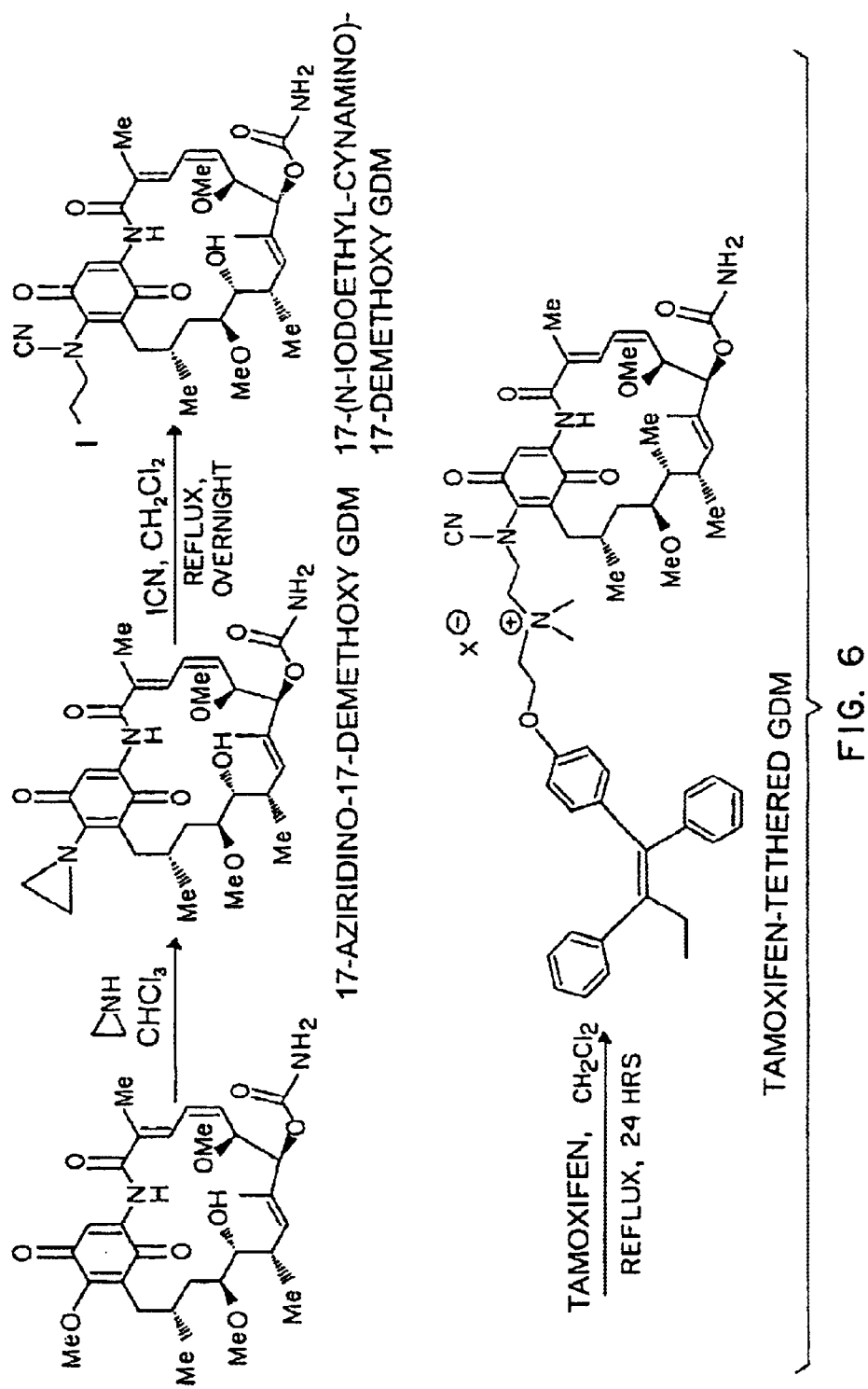
FIG. 6 shows a synthetic approach to making tamoxifen (TMX) tethered to GM with a spacer moiety.

FIG. 6 shows a synthetic approach to making tamoxifen (TMX) tethered to GM with a spacer moiety. In this case GM is reacted with aziridine to produce a novel GM analog 17-aziridino-17-demethoxygeldanamycin. This compound is reacted with cyanogen iodide (ICN) in refluxing methylene chloride to produce 17-(N-iodoethyl-N-cyano)-17-demethoxyGM. This GM analog has been found to bind to Hsp 90 as well as GM itself and is readily radiolabeled during synthesis through the use of radiolabeled ICN. The radiolabeled compound can be used in binding studies in place of geldanamycin. Corresponding 17-(N-iodoalkyl-N-cyano) compounds can be made by using azetidine (3 carbons), pyrrolidine (4 carbons) etc. in place of aziridine. Again, the same reaction can be used with herbimycin A, although a mixture of 17- and 19-substituted products is produced.

A further example of a compound in accordance with the invention is GM linked to the PI-3 kinase inhibitor wortmannin. In this case, an unsymmetrical diamine linker having a primary and a secondary amine is preferably used as the spacer. This is the case because the primary amine adds most quickly at the 17-position of GM, while the secondary amine reacts with the 21-position of the wortmannin furan ring to produce a product with the E orientation which has been shown to be more active than the Z orientation which is obtained upon reaction with a primary amine.

Figure 7A:
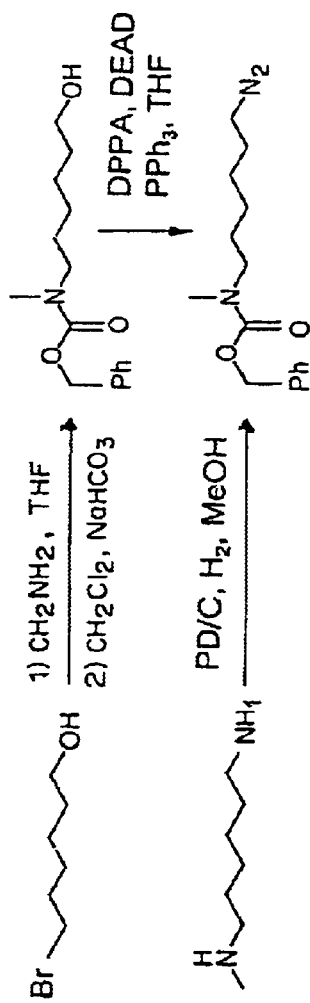
FIGS. 7A and 7B show the synthesis of a wortmannin-GM compound in accordance with the invention.

The unsymmetrical amine linker is prepared starting with 6-bromo-1-hexanol as shown in FIG. 7A. Displacement of the bromine with methylamine in THF followed by protection of the secondary amine provides an intermediate alcohol which is converted to the azide using DPPA, DEAD and $PPh_3$. Reduction of both the azido group and the benzyloxycarbonyl using Pd/C affords the 6-carbon unsymmetrical diamine.

Figure 7B:
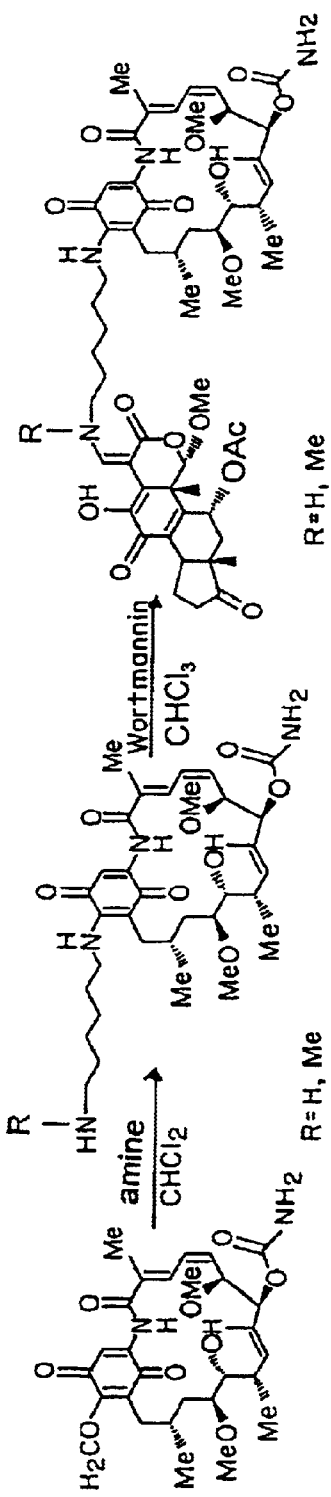

The unsymmetrical diamine is combined with GM in $CHCl_3$ to produce the intermediate GDN-diamine compound as shown in FIG. 7B. This compound is then reacted with wortmannin to produce the final wortmannin-tethered GM.

It will be appreciated by persons skilled in the art that these synthetic methodologies are easily adapted to other targeting moieties and to spacers of different lengths and compositions. All that is required is the presence of a reactive group in the targeting moiety which can be converted to an alkylamine or which will react with a primary or secondary amine which is part of a spacer previously attached to the ansamycin antibiotic.

EXAMPLE 1

Synthesis of Testosterone-GM

As show in FIG. 3, testosterone-tethered GM was prepared by reacting GM with a 17-alkylamino testosterone. The 17-alkylamino testosterone was prepared by adding octynyl tether in a convergent manner to monoprotected testosterone dione. The latter was prepared in two steps, according to literature procedures. The tether was synthesized starting from commercially available 6-bromohexanol.

6-bromohexanol (3 g, 16.6 mMoles) in 33 ml of anhydrous DMF, under argon atmosphere, was treated with imidazole (2.72 g, 40 mMoles) and the resulting homogeneous solution was cooled down to 0° C. then it was treated with TBSCl in 12 ml of DMF. Temperature was then allowed to warm up gradually to the ambient while reaction evolution was monitored by thin layer chromatography (TLC), silica gel ($SiO_2$) using ethylacetate (EtOAc)-hexane (Hex): 1-2 (v/v). After 2 hours at room temperature (rt) no starting material remained, and the reaction mixture was partitioned between water and EtOAc. After decantation, the aqueous layer was extracted with EtOAc thrice, and the combined organic layers were washed twice with $H_2O$, and brine, dried over $MgSO_4$, and concentrated under reduced pressure. The resulting yellowish oil was purified by short path silica gel column chromatography using EtOAc-Hex:1-4 as eluent to afford the desired silylether (4.4 g, 90% yield) as a colorless oil.

Lithium acetylide ethylene diamine complex (0.65 g, 6 mMoles) was added portionwise to anhydrous DMSO under inert atmosphere. The resulting not completely homogeneous dark brown mixture was cooled down to approximately 5° C., temperature at which the bromosilyl ether was introduced dropwise over 5 minutes. The cold bath was removed and reaction evolution was monitored by NMR of a quenched aliquot. After 5 hours at rt (usually an hour is enough) no starting material remained. The content of the flask was poured carefully into an Erlenmeyer flask containing ice. This was extracted with EtOAc thrice, and the combined organic layers were washed three times (3×) with water and once with brine. Brief drying over $MgSO_4$, and removal of the volatiles under reduced pressure gave a yellow oil. Purification by short path silica gel column chromatography, using EtOAc-Hex:1-19, gave 0.88 g (92% yield) of the desired true alkyne as a colorless oil.

A solution of the alkyne (80 mg, 0.33 mMole) in 1 ml of THF was cooled down to −78° C. under Argon, and it was treated with 0.22 ml of a 1.6 molar solution of n-butyl lithium in hexane. This was then warmed up to the ambient temperature for 20 minutes, then brought back to −78° C., temperature at which 0.2 ml of freshly distilled hexamethylphosphoramide (HMPA) was added, followed by monoprotected 17-ketotestosterone (80 mg, 0.24 mMole) as a suspension in 0.5 ml of THF. After an overnight stirring period at room temperature, the reaction was quenched with saturated ammonium chloride, decanted and extracted with EtOAc (3×). The combined organic layers were washed with brine, dried over $MgSO_4$, and concentrated under reduced pressure to give a light brown oily solid. Column chromatography on a short path $SiO_2$ column, using EtOAc-Hex: 1-9 gave the desired alcohol (50 mg, 36% yield) as a colorless oil.

The silylether (50 mg, 0.088 mMole) was diluted in 2 ml of anhydrous THF under argon. The resulting colorless solution was cooled down to 0° C., and it was treated with a one molar solution of tetrabutyl ammonium fluoride (115 microliters, 1.15 mMoles), and the cold bath was removed. After 3 hours at room temperature, no starting material remained. THF was removed under reduced pressure, and the residual brown oil was diluted in minimum chloroform and loaded on a short path $SiO_2$ column and eluted with EtOAc-Hex:1-2 to 1-1. This 34 mg (85% yield) of the alcohol as a colorless oil.

At 0° C., the Diol (34 mg, 0.0745 mMole) in 0.5 ml of methylene chloride, was treated with triethylamine (22.6 mg, 31 microliters, 0.22 mMoles) followed by mesylchloride (12.8 mg, 8 microliters, 0.11 mMoles). After half an hour at this temperature no starting material remained. The reaction mixture was then concentrated to dryness under vacuum, and it was dissolved in 2 ml of anhydrous DMF and then added with an excess (about 5 equivalents) of sodium azide and the resulting suspension was allowed to stir at room temperature for an overnight period. This was then partitioned between EtOAc and $H_2O$. After decantation, the aqueous layer was extracted with EtOAc (3×), then the combined organic layers were washed with water then brine, dried over $MgSO_4$, and concentrated under reduced pressure to leave a colorless oil. The desired azide 23 mg (64% yield for 2 steps) was isolated by short path $SiO_2$ column, using EtOAc-Hex: 1-4 as eluent.

The azido acetal (11 mg, 0.0228 mMole) in 2 ml of methanol was treated with 0.5 ml of 1.0 normal hydrochloric acid, at rt. for 3 hours. pH was made alkaline (7–8) by careful addition of saturated sodium bicarbonate, and methanol was removed under vacuum. The remaining white oily solid was extracted with $CHCl_3$ until TLC indicated no organic material was present in the aqueous phase. The combined organic layers were dried briefly over $MgSO_4$, and evaporated under vacuum to give an oily solid film. This was dissolved in minimum $CHCl_3$, and loaded on a short $SiO_2$ plug and eluted with EtOAc-Hex: 1-4. This gave 9 mg (90% yield) of the desired azido enone as a colorless film.

At room temperature, the azide (33 mg, 0.0755 mMole) in 1 ml of anhydrous THF, was treated with 0.23 ml (0.23 mMole) of a 1.0 molar solution of triethylphosphine in THF. Reaction evolution was monitored by TLC; $SiO_2$, EtOAc-Hex: 1-1. Within 1 hour, the reaction was over. This was then treated with 0.23 ml of water and stirring was continued for overnight period. The slightly yellowish reaction mixture was evaporated to dryness, under high vacuum to yield a yellowish film. This taken in $H_2O$ and ether while pH was made basic with concentrated ammonia. Following decantation, the aqueous phase was extracted thrice with ether, and the combined organic layers were in turn extracted three times with 1.0 N HCl. The combined HCl extracts were then brought to basic pH with ammonia, and extracted with $CHCl_3$ until the aqueous phase gave a negative ninhydrin test. The combined chloroform layers were then dried briefly over $MgSO_4$, and concentrated under reduced pressure to give a yellowish film (24.6 mg).

Testosterone-GM product was obtained by reacting geldanamycin (5.6 mg, 10 micromoles) with crude 17-alpha-(8-amino-1-octynyl)-testosterone (24.5 mg, 60 micromoles) in 0.5 ml of anhydrous DMSO at room temperature, and in the dark. After 12 hours, the initially yellow solution turned deep purple. The reaction mixture was then partitioned between $CHCl_3$ and $H_2O$. Following decantation, the aqueous phase was extracted with $CHCl_3$ (5×). The combined organic layers were then washed with water (3×), dried over freshly ground sodium sulfite, filtered and evaporated under reduced pressure. The residual oil (contains DMSO) was loaded on a short $SiO_2$ plug and the desired material was purified using the gradient elution system, methanol 2 to 10% in chloroform. This gave the desired drug (3.4 mg, 36% yield) as a purple solid.

EXAMPLE 2

Figure 8A:
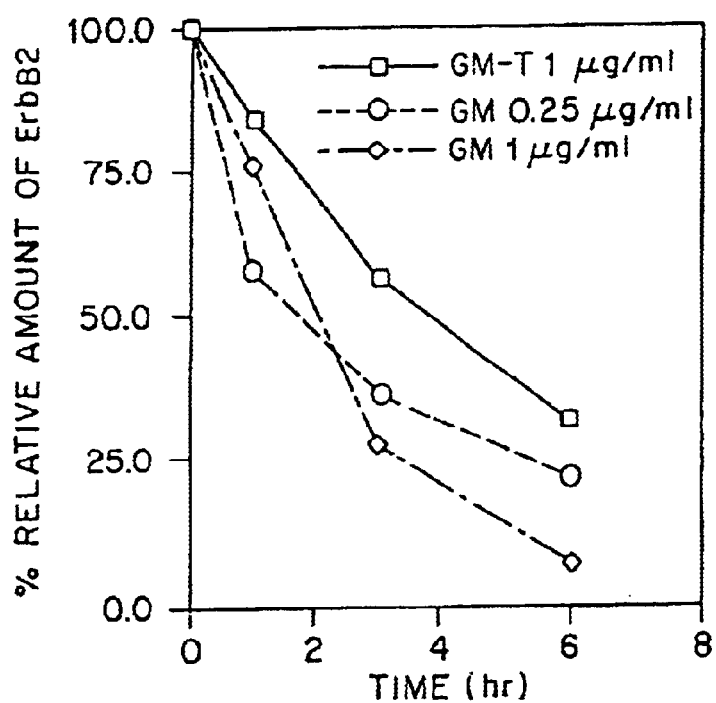
FIGS. 8A and 8B shows levels of ErbB2 and androgen receptors in prostate cancer cells after exposure to geldanamycin or to testosterone-tethered geldanamycin.
Figure 8B:
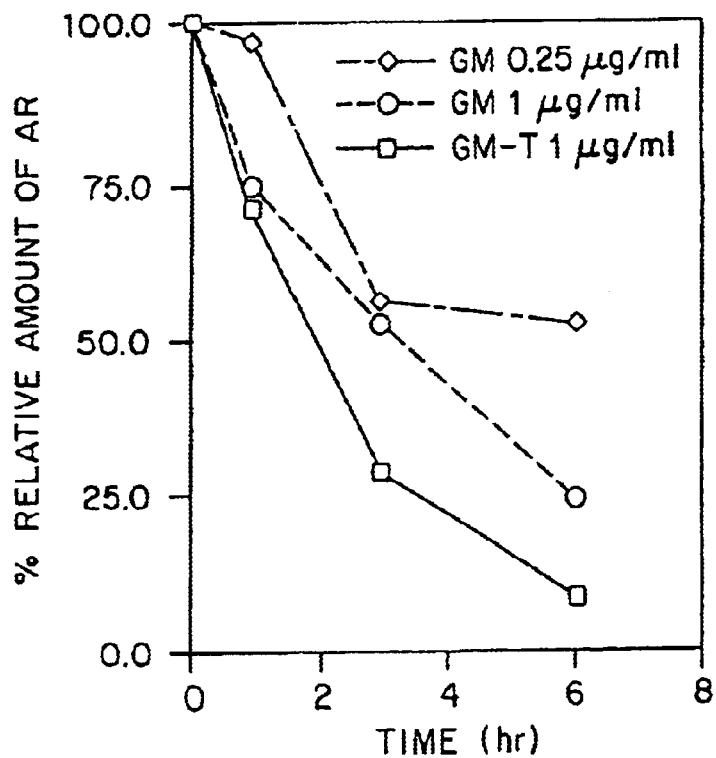

A prostate cancer cell line (LN-CAP) was exposed in culture medium to geldanamycin alone at levels of 0.25 and 1 ug/ml and to testosterone tethered GM (GM-T) synthesized as in Example 1. The cells were monitored by immunoblotting for the presence of ErbB2 a tyrosine kinase which is known to be degraded as a result of exposure to GM and for the presence of androgen receptors. All three treatments reduced the levels of ErbB2 over time, but the least reduction was observed for cells treated with GM-T. (FIG. 8A) In contrast, the greatest reduction in the amount of androgen receptors was observed in the cells treated with GM-T. (FIG. 8B). Thus, the GM-T exhibited the desired targeting and specificity for androgen receptors.

EXAMPLE 3

Synthesis of Estradiol Tethered GM

As shown in FIG. 5, the synthesis is to a large extent similar to that of testosterone tethered GM, though improvements are under way at this time. Tertiary butyldimethylsilyloxy estrone was condensed with the dilithium anion of 1-hexyne-6-ol in THF at −78° C. to afford the corresponding 17-(1-hydroxy hexynyl)estradiol in moderate yield. Mesylation, azide displacement, deprotection of the phenolic alcohol, and reduction of the azide into the primary amine gave the desired intermediate for coupling with GM. This was done in DMSO at rt., in the dark to afford a new 6 carbon tethered GM to estradiol. The 8 carbon tethered analog was done in the same manner as for testosterone.

EXAMPLE 4

Figure 9A:
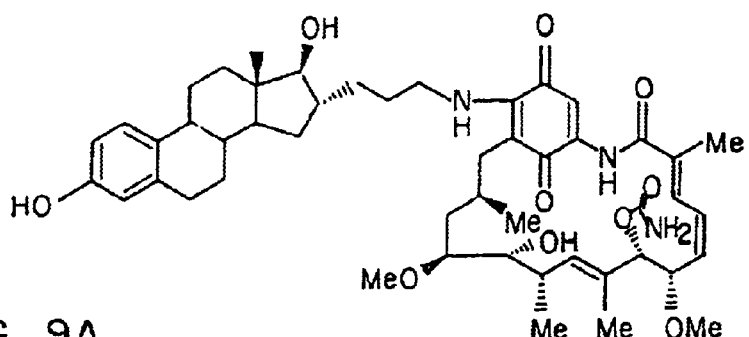
FIGS. 9A–9G show the structures of various geldanamycin-estradiol compounds in accordance with the invention.
Figure 9B:
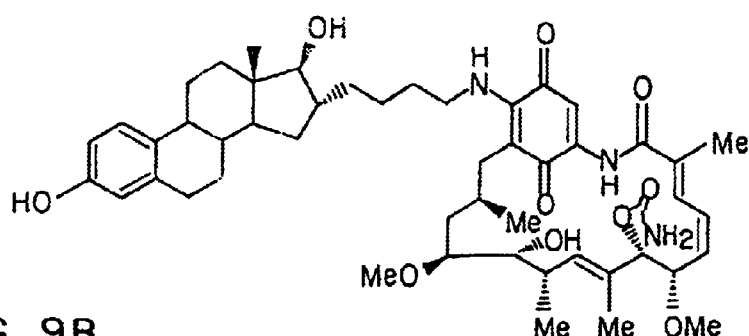
Figure 9C:
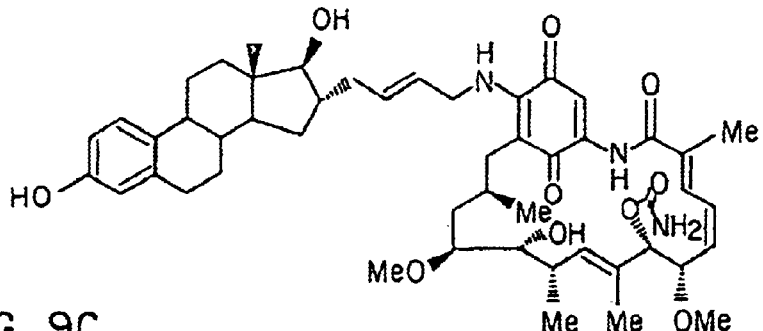
Figure 10:
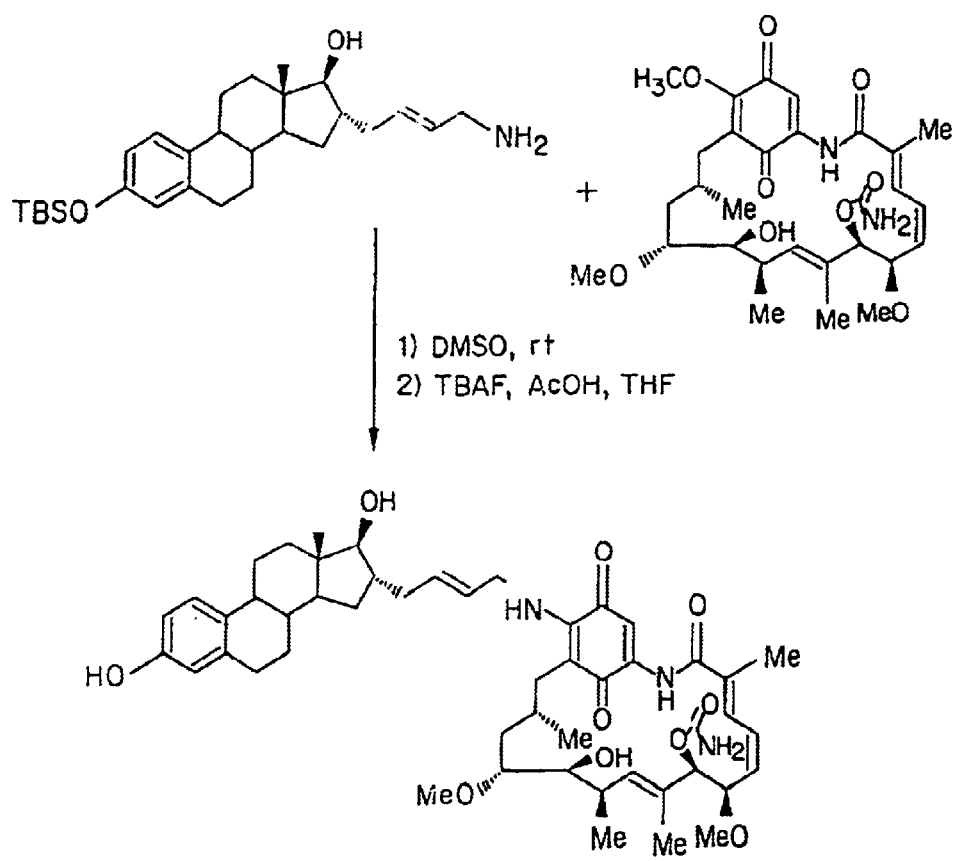
FIG. 10 shows a reaction scheme for synthesis of a GM-4-estradiol hybrid.

An estradiol-geldanamycin hybrid with a 4-carbon tether containing a double bond (FIG. 9C) was synthesized as shown in FIG. 10. Amine (40 mg, prepared from the published procedure by Katzenellenbogen et al. *J. Org. Chem.* (1987) 52, 247.) was dissolved in 1 mL of DMSO and 20 mg of Geldanamycin was added. The mixture was allowed to stir overnight, concentrated in vacuo and purified by chromatography on silica gel to afford a purple solid. This material (17 mg) was then dissolved 1.5 mL of THF and 2 drops of AcOH followed by 0.02 mL of TBAF (tetra-n-butyl ammonium fluoride, 1.0 M in THF) was added and the mixture was allowed to stir overnight. The reaction mixture was then concentrated and purified by chromatography on silica gel to afford 13 mg of the hybrid as a purple film.

Figure 9D:
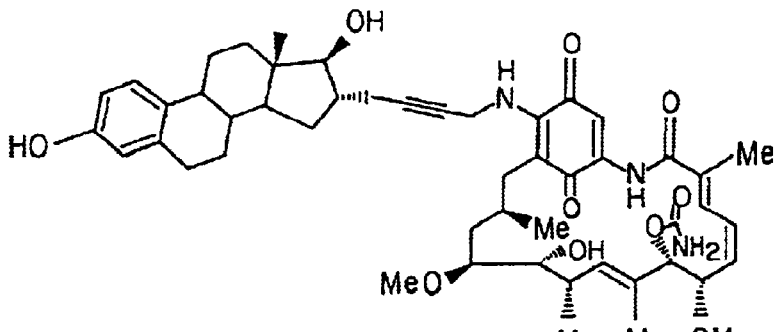
Figure 9E:
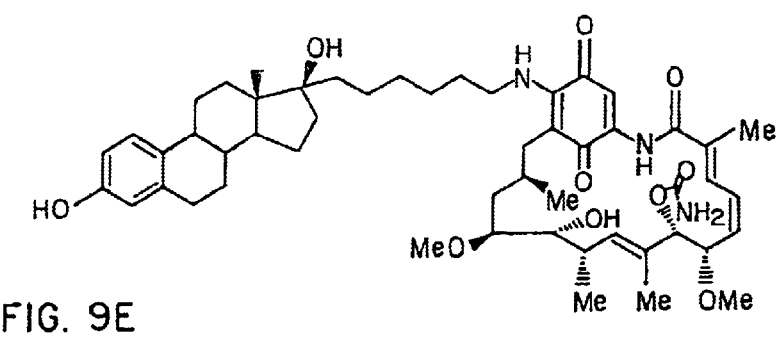
Figure 9F:
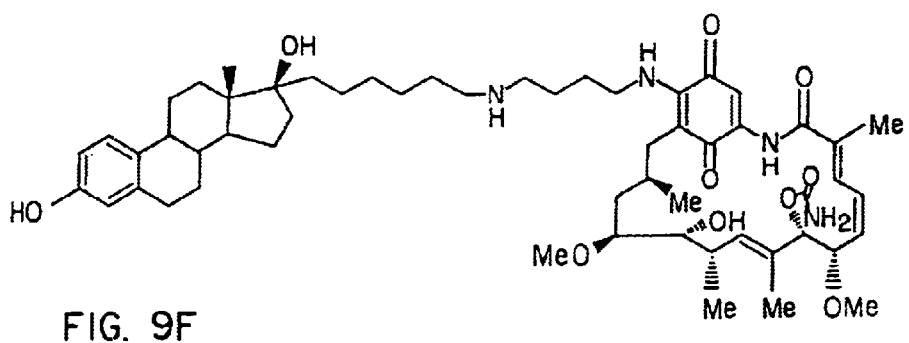
Figure 9G:
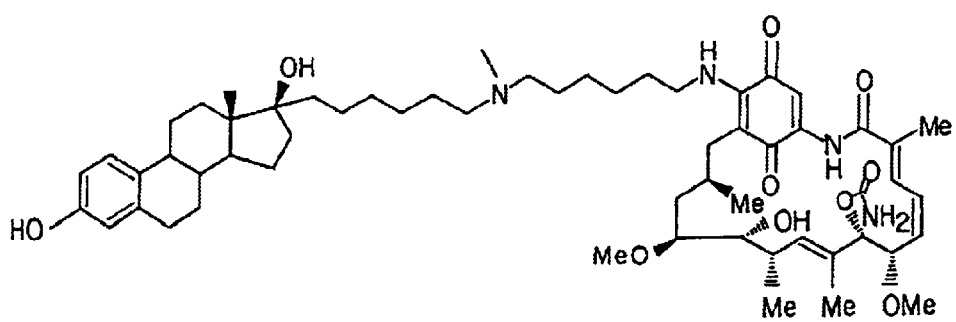

The activity of this compound was compared with the activity of other GM-estradiol compounds as shown in FIGS. 9F and 9G. The effects of these compounds on receptor of various types were evaluated by exposing MCF-7 breast cancer cells, in vitro, to 1 $\mu$M levels of the compounds for varying periods of time, and then testing for the presence of the receptor using receptor-specific antibodies in an immunoblotting experiment. The results are summarized in Table 1, where GM-4-E2 indicates a geldanamycin-estradiol compound with a 4-carbon tether. A + in the table indicates that the receptor was detected by immunoblotting, a − indicates that it was not detectable, and a ± indicates a weak or equivocal result.

The results show that compounds with longer tethers are less active, although whether this is a function of tether length or the different substitution position in the estradiol has not been determined. Nevertheless, all of the compounds in accordance with the invention show increased selectivity for estrogen receptors and ErbB2 receptors compared to geldanamycin alone. This selectivity is most pronounced in GM-4-E2.

TABLE 1

| | | Exposure Time (hours) | | | | |
|---|---|---|---|---|---|---|
| Drug | Receptor | 0 | 3 | 6 | 12 | 24 |
| GM | ErbB2 | + | − | − | − | − |
| | Raf-1 | + | + | + | − | − |
| | estrogen receptor | + | − | − | − | − |
| GM-4-E2 | ErbB2 | + | ± | − | − | − |
| | Raf-1 | + | + | + | + | + |

TABLE 1-continued

| Drug | Receptor | Exposure Time (hours) | | | | |
|---|---|---|---|---|---|---|
| | | 0 | 3 | 6 | 12 | 24 |
| | estrogen receptor | + | ± | − | − | − |
| GM-10-E2 | ErbB2 | + | + | + | + | − |
| | Raf-1 | + | + | + | + | + |
| | estrogen receptor | + | + | + | ± | + |
| GM-13-E2 | ErbB2 | + | + | + | + | − |
| | Raf-1 | + | + | + | + | + |
| | estrogen receptor | + | + | + | ± | − |

EXAMPLE 5

The immunoblotting experiment of Example 4 was repeated using just geldanamycin and GM-4-E2, but including insulin-like growth factor 1 receptor (IGF1-R) in the panel of proteins tested for. The results are summarized in Table 2. The same pattern of activity is observed, with GM-4-E2 being less injurious to IGF1-R than geldanamycin alone.

TABLE 2

| Drug | Receptor | Exposure Time (hours) | | | |
|---|---|---|---|---|---|
| | | 0 | 6 | 12 | 24 |
| GM | ErbB2 | + | − | − | − |
| | Raf-1 | + | + | − | − |
| | estrogen receptor | + | − | − | − |
| | IGFI-R | + | + | + | − |
| GM-4-E2 | ErbB2 | + | ± | − | − |
| | Raf-1 | + | + | + | + |
| | estrogen receptor | + | − | − | − |
| | IGFI-R | + | + | + | + |

EXAMPLE 6

The immunoblotting experiment of example 4 was repeated using a prostate cancer cell line, LNCaP, to determine the affect of GM-4-E2 on androgen receptors. The results are summarized in Table 3. Geldanamycin alone destroys these receptors, GM-4-E2 does not.

TABLE 3

| Drug | Receptor | Exposure Time (hours) | | | | |
|---|---|---|---|---|---|---|
| | | 0 | 3 | 6 | 12 | 24 |
| GM | ErbB2 | + | + | − | − | − |
| | androgen receptor | + | + | + | + | − |
| GM-4-E2 | ErbB2 | + | + | + | − | − |
| | androgen receptor | + | + | + | + | + |

EXAMPLE 7

The compounds of FIGS. 9A–9G have been tested for activity with respect to erbB2 (Her2), raf-1 and estrogen receptors. The relative activities are summarized in Table 4, where ++++ is most active and − is minimal activity.

TABLE 4

| Compound | ErbB2 (Her2) | raf-1 | estrogen receptor |
|---|---|---|---|
| FIG. 9A | + | + | + |
| FIG. 9B | − | − | + |
| FIG. 9C | +++ | − | ++++ |
| FIG. 9D | + | − | ++ |
| FIG. 9E | ++ | − | + |
| FIG. 9F | + | − | + |
| FIG. 9G | + | − | + |
| geldanamycin | ++++ | ++++ | ++++ |

EXAMPLE 8

Synthesis of Tamoxifen Tethered GM

We have decided to use the amino group of tamoxifen as not only a potential entity for connection with a halide (preferably an iodide—to accommodate for the safety of GM during the quaternization of the amine—that could be changed at will into another halide, Cl, Br, or another counter ion on an ion exchange resin), but also to further increase the water solubility of the analog by creating a charge in the tether. To do so we required a GM analog with a primary iodide. This was not an easy task, since iodoalkylamines are not stable and could not be used in a single step type of strategy. Usually, one has to use the aminoalcohol and introduce the iodide later, which is not compatible with the presence of GM. We have found that the Von Braun reaction on a cyclic amine could lead to that precise iodoalkylamine connected to GM in good yield.

Synthesis of the aminoGM: At room temperature, GM (10 mg, 17.85 micromoles) was dissolved in 1 ml of chloroform. The resulting yellow solution was treated with aziridine (100 mg) in 1 ml of $CHCl_3$. This was allowed to stir in the dark for 2 hours. The reaction became orange, and the whole reaction mixture was loaded on a short path silica gel column, and the desired material (10 mg, 98% yield)was isolated as an orange solid.

Azetidine can be used in place of aziridine to make a longer tether. Azetidine can be made following the literature procedure (R. C. Schnur, et al, *J. Med. Chem.*, 38, 3806, 1995). Similarly 5.6 mg (10 micromoles) of GM were reacted with 30 microliters of pyrrolidine in 0.5 ml of chloroform to give after an hour at room temperature 5 mg (83% yield) of the 17-demethoxy-17-pyrrolidino GM as a deep purple film.

Synthesis of 17-N-Iodoalkyl-N-cyanoGM analogs: In a typical experiment, 2.5 mg (4.38 micromoles) of 17-aziridino GM were dissolved in 0.25 ml of anhydrous 1,2-dichloroethane. The resulting orange solution was treated with cyanogen iodide (3 mg, 19.6 micromoles), and the reactivial was sealed with a Teflon cap. Temperature was then brought up to 65–70° C. for 12 hours in the dark. The reaction mixture became light purple. This was loaded on a short silica gel plug and the desired material 3 mg (94% yield) was isolated as a light purple film, using methanol 5–10% in chloroform gradient elution system.

Similarly 5 mg (8.34 micromoles) of 17-pyrrolidino GM were reacted with 4 equivalents of cyanogen iodide in 1,2-dichloroethane at 65° C. for 36 hours to give 5 mg (80% yield) of the iodobutyl analog.

Synthesis of tamoxifen tethered GM analogs: In atypical experiment, 3 mg (4.14 micromoles) of 17-N-Iodoethyl-N-cyanoGM were dissolved in 0.5 ml of anhydrous acetonitrile under argon atmosphere. The resulting purple solution was treated with 1.6 mg (4.14 micromoles ) of tamoxifen. This gave a suspension that was sealed in a reactivial and heated up to 75° C. for 18 hours. Reaction evolution was monitored by TLC, SiO2, using 10% methanol in chloroform. The lightly purple color reaction mixture was then cooled down to 0° C., and filtered while cold. The product was washed with cold acetonitrile into a light purple solid. The product from the N-iodobutyl analog required higher temperature (refluxing benzene for 12 hours).

EXAMPLE 9

Starting with herbimycin A in place of the geldanamycin and reacting with aziridine, azetidine, pyrrolidine as in Example 7 would give the corresponding 17- and 19-amino herbimycin A compounds. These are separated by silica gel chromatography. The action of cyanogen iodide on these compounds provides the corresponding 17-N-Cyano-N-iodoalkylamine and 19-N-Cyano-N-iodoalkylamine herbimycin A. Their reactions with tamoxifen under the same conditions as for GM leads to the corresponding ammonium salts of tamoxifen.

EXAMPLE 10
Synthesis of Wortmannin Tethered GM

Primary Diamine: To a solution of geldanamycin (3 mg, 0.0053 mmol) in 0.5 mL of $CHCl_3$ was added 6.2 mg (10 eq.) of hexamethylenediamine in the dark for 1 hr. The reaction mixture was then washed with 4×500 uL of water and concentrated under high vacuum for 30 minutes to afford a purple solid. This material was dissolved in 0.25 mL of $CH_2Cl_2$ and 2.2 mg (0.0053 mmol) of wortmannin was added in the dark at room temperature. After two hours the brown-orange reaction mixture was applied directly to chromatography on silica gel eluting with 5% MeOH in $CH_2Cl_2$ to afford 1.5 mg (27%) of the geldanamycin-wortmannin hybrid as a yellow-brown film.

Unsymmetrical Primary/Secondary diamine: 6-(N-methyl-N-Carbobenzyloxyamino)-hexan-1-ol was synthesized as follows. To a solution of 6-bromo-hexan-1-ol (2.0 g, 17.4 mmol) was added 50 mL of a 2.0 M solution of methylamine (~10 eq.) in THF and the reaction was allowed to stir overnight. The reaction mixture was diluted with 30 mL of ether, filtered, and concentrated. The crude material was then diluted in 30 mL of ether and 50 mL of saturated $NaHCO_3$ solution. Carbobenzyloxychloride (2.5 g, 51 mmol) was then added and the reaction mixture was stirred vigorously for 2 hours. The reaction was then diluted with 100 mL of ether, washed with brine, dried over $MgSO_4$, filtered and concentrated. Silica gel chromatography (10–50% EtOAc:hexanes) afforded 3.1 g (76%) of product as a clear oil.

6-Azido-1-(N-methyl-N-Carbobenzyloxyamino) was then synthesized by forming a solution of the alcohol (1.52 g, 6.4 mmol) with triphenylphosphine (2.18 g, 8.3 mmol), and diethylazidodicarboxylate (1.45 g, 8.3 mmol) in 20 mL of THF and adding diphenylphosphorylazide (1.79 mL, 8.3 mmol) dropwise over 15 minutes and the reaction was allowed to stir overnight. The reaction mixture was concentrated and purified via silica gel chromatography (10–30% EtOAc:hexanes) to afford 1.07 g (75%) of a white-yellow solid.

6-amino-1-(N-methylhexylamine) was synthesized from the azide as follows. A solution of the azide 750 mg (2.25 mmol) and 100 mg of 10% Pd/C in 5 mL of MeOH was hydrogenated under 20 psi of $H_2$ at 45° C. for 48 hours. The reaction mixture was filtered through celite and concentrated to afford the diamine as a yellow oil. This material is used to prepare a geldanamycin-wortmannin hybrid using the procedure described above for primary diamines.

EXAMPLE 11

Figure 11:
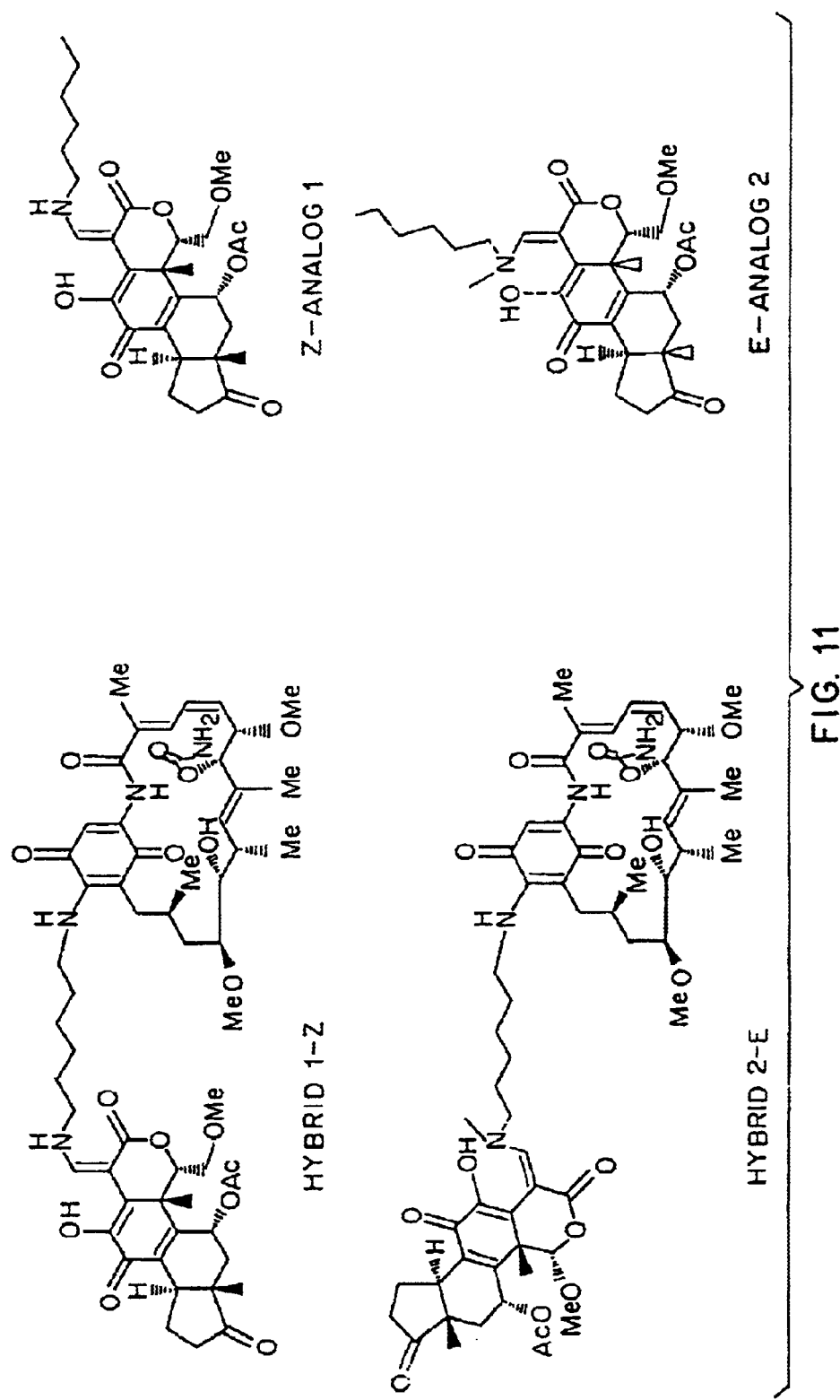
FIG. 11 shows structures of structures of wortmannin isomeric forms, and of geldanamycin-wortmannin hybrid compounds in accordance with the invention.
Figure 12:
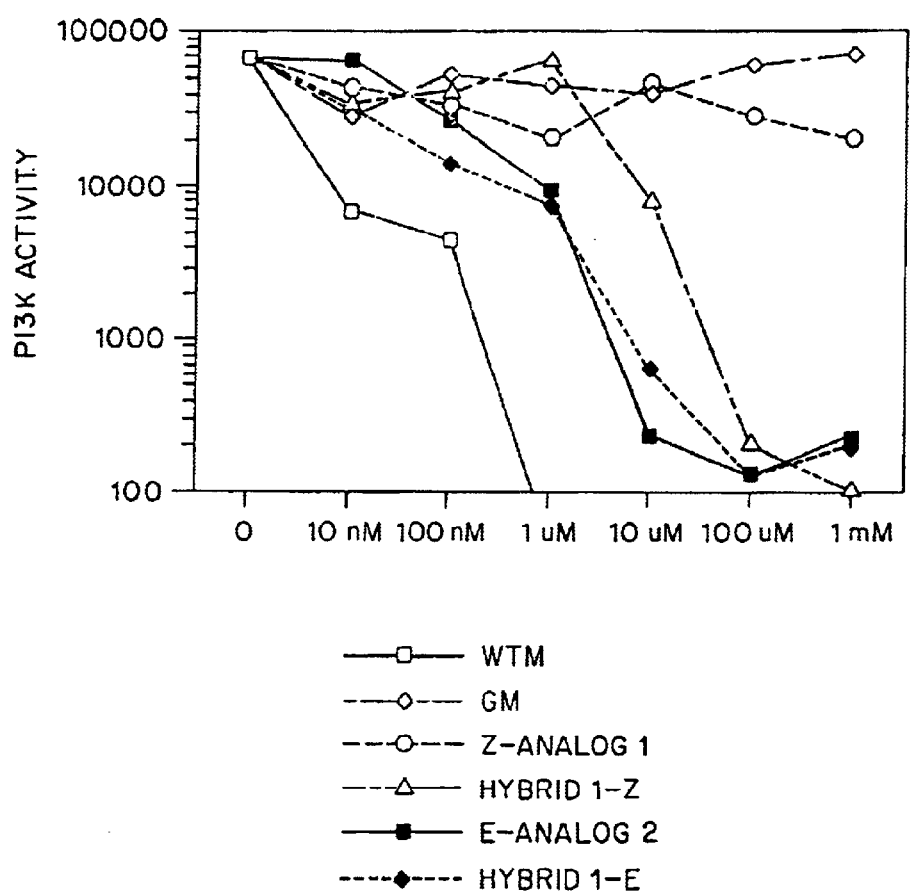
FIG. 12 shows the inhibition of PI3 kinase by various compounds.

Wortmannin analogs were prepared with the tether linked to the amino group of the opened furan in either of two isomeric orientations, and these were designated as Z-analog 1 and an E-analog 2 as shown in FIG. 11. Each of these compounds was coupled to geldanamycin to form hybrid compounds in accordance with the invention (See, FIG. 11). These compounds were tested for inhibition of PI3 kinase activity. The results are summarized in FIG. 12. As is known from the art, wortmannin alone inhibits PI3 kinase activity, as does the E-analog 2. The Z-analog 1, however is inactive, as is geldanamycin alone. Surprisingly, however, substantial PI3 kinase inhibition is observed for both hybrid compounds. Thus, a hybrid compound formed from two inactive species is capable of providing significant inhibition of PI3 kinase, substantiating the belief that the mechanism of action of the compounds of the invention is not a simple interaction of one portion of molecule with a normal target, but rather a synergistic interaction in which both parts of the hybrid molecule play an important role. Further, these results establish the effectiveness of the compounds of the invention against targets which are not normally subject to degradation by geldanamycin.

We claim:

1. A chemical compound comprising
    a targeting moiety which specifically binds to a protein, receptor or marker; and
    an hsp-binding moiety which binds to the pocket of hsp90 with which ansamycin antibiotics bind.

2. The chemical compound according to claim 1, wherein the targeting moiety specifically binds to a hormone receptor.

3. The chemical compound according to claim 2, wherein the targeting moiety specifically binds to an androgen receptor.

4. The chemical compound according to claim 3, wherein the targeting moiety is testosterone.

5. The chemical compound according to claim 2, wherein the targeting moiety specifically binds to an estrogen receptor.

6. The chemical compound according to claim 5, wherein the targeting moiety is selected from the group consisting of estrogen, estradiol and tamoxifen.

7. The chemical compound according to claim 1, wherein the targeting moiety specifically binds to erbB (HER2) receptors.

8. The chemical compound according to claim 1, wherein the targeting moiety is selected from wortmannin or derivatives thereof.

9. The chemical compound according to claim 8, wherein the targeting moiety is a Z analog of wortmannin.

10. The chemical compound of claim 1, wherein the hsp-binding moiety is an ansamycin antibiotic.

11. The chemical compound according to claim 10, wherein the targeting moiety specifically binds to a hormone receptor.

12. The chemical compound according to claim 10, wherein the targeting moiety specifically binds to an androgen receptor.

13. The chemical compound according to claim 10, wherein the targeting moiety specifically binds to an estrogen receptor.

14. The chemical compound according to claim 10, wherein the targeting moiety is selected from the group consisting of estrogen, estradiol and tamoxifen.

15. The chemical compound of claim 7, wherein the hsp-binding moiety is an ansamycin antibiotic.

16. The chemical compound of claim 10, wherein the ansamycin antibiotic is geldanamycin.

17. The chemical compound of claim 16, wherein the ansamycin antibiotic is herbimycin A.

18. The chemical compound according to claim 10, further comprising a spacer moiety disposed between the targeting moiety and the ansamycin antibiotic.

19. A method for targeted destruction of cancer cells requiring a protein, receptor or marker for viability, comprising administering to the cells a chemical compound comprising a targeting moiety which specifically binds to a protein, receptor or marker and an hsp-binding moiety which binds to the pocket of hsp90 with which ansamycin antibiotics bind.

20. The method according to claim 19, wherein the targeting moiety specifically binds to a hormone receptor.

21. The method according to claim 19, wherein the hormone receptor is an androgen receptor or an estrogen receptor.

22. The method according to claim 19, wherein the targeting moiety specifically binds to erbB (HER2) receptors.

23. The method according to claim 19, wherein the hsp-binding moiety is an ansamycin antibiotic.

24. The method according to claim 19, further comprising a spacer moiety disposed between the targeting moiety and the ansamycin antiboitic.

25. A method for targeted destruction of a protein in a cell, comprising administering to the cell a chemical compound comprising a targeting moiety which specifically binds to the protein and an hsp-binding moiety which binds to the pocket of hsp90 with which ansamycin antibiotics bind.

26. The method according to claim 25, wherein the targeting moiety specifically binds to a hormone receptor.

27. The method according to claim 25, wherein the targeting moiety specifically binds to an androgen receptor or an estrogen receptor.

28. The method according to claim 25, wherein the targeting moiety specifically binds to erbB (HER2) receptors.

29. The method according to claim 25, wherein the hsp-binding moiety is an ansamycin antibiotic.

30. The method according to claim 25, further comprising a spacer moiety disposed between the targeting moiety and the ansamycin antiboitic.

31. A method for synthesizing a chemical compound comprising a targeting moiety which specifically binds to a receptor or marker and an ansamycin antibiotic, comprising reacting the ansamycin antibiotic with an alkylamine derivative of the targeting moiety.

32. The method of claim 31, wherein the ansamycin antibiotic is herbimycin A.

33. The method of claim 31, wherein the ansamycin antibiotic is geldanamycin.

34. 17-(N-iodoalkyl-N-cyano)-17-demethoxy geldanamycin.

35. A method for treating cancer comprising administering to a subject suspected to have cancer a therapeutic composition comprising a chemical compound comprising a targeting moiety which specifically binds to a protein, receptor or marker and an hsp-binding moiety which binds to the pocket of hsp90 with which ansamycin antibiotics bind.

36. The method according to claim 35, wherein the targeting moiety specifically binds to a hormone receptor.

37. The method according to claim 36, wherein the targeting moiety specifically binds to an androgen receptor or an estrogen receptor.

38. The method according to claim 35, wherein the targeting moiety specifically binds to erbB (HER2) receptors.

39. The method according to claim 35, wherein the hsp-binding moiety is an ansamycin antibiotic.

40. The method according to claim 35, further comprising a spacer moiety disposed between the targeting moiety and the ansamycin antiboitic.

\* \* \* \* \*

UNITED STATES PATENT AND TRADEMARK OFFICE
CERTIFICATE OF CORRECTION

PATENT NO.   : 6,670,348 B1
DATED        : December 30, 2003
INVENTOR(S)  : Rosen et al.

It is certified that error appears in the above-identified patent and that said Letters Patent is hereby corrected as shown below:

Column 1,
Line 7, insert the following text -- This invention was made under a federal support contract (DAMD 17-97-1-7213) with the United States Army. The United States may have certain rights in this invention. --

Signed and Sealed this

Third Day of May, 2005

JON W. DUDAS
*Director of the United States Patent and Trademark Office*

UNITED STATES PATENT AND TRADEMARK OFFICE
CERTIFICATE OF CORRECTION

| | |
|---|---|
| PATENT NO. | : 6,670,348 B1 |
| APPLICATION NO. | : 09/403434 |
| DATED | : December 30, 2003 |
| INVENTOR(S) | : Rosen et al. |

It is certified that error appears in the above-identified patent and that said Letters Patent is hereby corrected as shown below:

Column 1, Line 7: This application was supported by ARMY grant number DAMD17-97-1-7213. The United States government has certain rights in this invention.

Signed and Sealed this

Twenty-sixth Day of August, 2008

JON W. DUDAS
*Director of the United States Patent and Trademark Office*